(12) United States Patent
Lastovich et al.

(10) Patent No.: US 6,808,506 B2
(45) Date of Patent: Oct. 26, 2004

(54) DEVICE AND METHOD FOR DELIVERING OR WITHDRAWING A SUBSTANCE THROUGH THE SKIN

(75) Inventors: Alexander G. Lastovich, Raleigh, NC (US); James K. Fentress, Morrisville, NC (US); Julia Griggs, Morrisville, NC (US); Ronald J. Pettis, Cary, NC (US); Diane Sutter, Cary, NC (US); Frank E. Martin, Durham, NC (US); M. Ishaq Haider, Morrisville, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 34 days.

(21) Appl. No.: 10/357,502

(22) Filed: Feb. 4, 2003

(65) Prior Publication Data

US 2003/0220610 A1 Nov. 27, 2003

Related U.S. Application Data

(60) Provisional application No. 60/353,194, filed on Feb. 4, 2002, provisional application No. 60/397,038, filed on Jul. 22, 2002, provisional application No. 60/407,284, filed on Sep. 3, 2002, provisional application No. 60/420,233, filed on Oct. 23, 2002, provisional application No. 60/377,649, filed on May 6, 2002, and provisional application No. 60/389,881, filed on Jun. 20, 2002.

(51) Int. Cl.$^7$ ............................................... A61B 17/20
(52) U.S. Cl. ......................................................... 604/47
(58) Field of Search ............................. 604/46, 47, 506; 606/186; 600/583; 424/449

(56) References Cited

U.S. PATENT DOCUMENTS 3,086,530 A  *  4/1963  Groom ........................ 606/186
3,595,231 A       7/1971  Pistor
4,886,499 A      12/1989  Cirelli et al.
5,250,023 A      10/1993  Lee et al.
5,527,288 A       6/1996  Gross et al.
5,879,326 A       3/1999  Godshall et al.
5,997,501 A      12/1999  Gross et al.
6,024,706 A  *   2/2000  Hsiao ......................... 600/556
6,183,434 B1      2/2001  Eppstein
6,494,865 B1     12/2002  Alchas
6,629,949 B1  * 10/2003  Douglas ....................... 604/46

FOREIGN PATENT DOCUMENTS

WO        WO 97/48440 A1    12/1997

* cited by examiner

*Primary Examiner*—Sharon Kennedy
(74) *Attorney, Agent, or Firm*—Becton, Dickinson and Company; Chad C. Anderson, Esq.

(57) ABSTRACT

An apparatus for delivering or withdrawing a fluid through at least one layer of the skin is provided. A device includes a body having a top face, a bottom face, a side edge and at least one channel. The bottom face includes a first surface area and a second surface area adjacent to and recessed at a first distance from the first surface area. The bottom face further includes at least one raised protrusion disposed on the second surface area. The protrusion has a height from the first surface greater than the first distance. At least one dermal-access member is provided in the protrusion and is in fluid communication with the channel to deliver or withdraw the fluid. The dermal-access member extends at least 1 mm from the protrusion. A mechanism drives the device against the skin at a calculated speed of about 6 m/s to about 18 m/s.

9 Claims, 20 Drawing Sheets

FIG. 17

CONSTANT PRESSURE: 15PSI; 50uL AIR BOLUS; 1mm NEEDLES

SMALL 0.0375'd CONE GEOMETRY

| CONE | OVER | EXP | LEAKER | BLEB TYPE | AVG RATE (144 min.) | IF NO LEAKS |
|---|---|---|---|---|---|---|
| SMALL | 0 | · | Y | | 0 | |
| SMALL | 0 | 10 | N | 3 | 61.1 | 61.1 |
| SMALL | 0 | · | Y | | 0 | |
| SMALL | 0 | 15 | N | 3 | 46.6 | 46.6 |
| SMALL | 0 | · | Y | | 0 | |
| SMALL | 0 | 29 | N | 3 | 29.1 | 29.1 |
| SMALL | 0 | · | Y | | 0 | |
| | | | | AVERAGE | 19.54 | 45.60 |
| | | | | STDEV | 26.07 | 16.02 |
| SMALL | 20 | 2 | N | 3 | 12.6 | 12.6 |
| SMALL | 20 | 7 | N | 3 | 46.9 | 46.9 |
| SMALL | 20 | 11 | N | 3 | 62.4 | 62.4 |
| SMALL | 20 | 16 | N | 2 | 12.7 | 12.7 |
| SMALL | 20 | 20 | N | 3 | 66.8 | 66.8 |
| SMALL | 20 | 21 | N | 3 | 8.4 | 8.4 |
| SMALL | 20 | 32 | N | 3 | 31.7 | 31.7 |
| SMALL | 20 | 37 | N | 3 | 22.8 | 22.8 |
| | | | | AVERAGE | 33.04 | 33.04 |
| | | | | STDEV | 23.11 | 23.11 |
| SMALL | 40 | 5 | N | 3 | 173.5 | 173.5 |
| SMALL | 40 | 12 | N | 3 | 30.7 | 30.7 |
| SMALL | 40 | 19 | N | 3 | 22.8 | 22.8 |
| SMALL | 40 | 24 | N | 3 | 54.3 | 54.3 |
| SMALL | 40 | 30 | N | 1BIG, 2SM | 29.6 | 29.6 |
| SMALL | 40 | 33 | N | 3 | 18.7 | 18.7 |
| | | | | AVERAGE | 54.93 | 54.93 |
| | | | | STDEV | 59.39 | 59.39 |

CONSTANT PRESSURE: 15PSI; 50uL AIR BOLUS; 1mm NEEDLES

REGULAR 0.075'd CONE GEOMETRY

| CONE | OVER | EXP | LEAKER | BLEB TYPE | AVG RATE (144 min.) | IF NO LEAKS |
|---|---|---|---|---|---|---|
| REG | 0 | · | Y | | 0 | |
| REG | 0 | · | Y | | 0 | |
| REG | 0 | 17 | N | 3 | 67.5 | 67.5 |
| REG | 0 | 23 | N | 3 | 44.2 | 44.2 |
| REG | 0 | · | Y | | 0 | |
| REG | 0 | · | Y | | 0 | |
| REG | 0 | · | Y | | 0 | |
| | | | | AVERAGE | 15.96 | 55.85 |
| | | | | STDEV | 28.07 | |
| REG | 20 | · | Y | | 0 | |
| REG | 20 | 18 | N | 3 | 42.4 | 42.4 |
| REG | 20 | 25 | N | 3 | 110.8 | 110.8 |
| REG | 20 | 31 | N | 3 | 27.2 | 27.2 |
| REG | 20 | 38 | N | 3 | 50.1 | 50.1 |
| | | | | AVERAGE | 46.10 | 57.63 |
| | | | | STDEV | 40.92 | 36.70 |
| REG | 40 | 4 | N | 3 | 31.7 | 31.7 |
| REG | 40 | · | Y | | 0 | |
| REG | 40 | 13 | N | 3 | 156.2 | 156.2 |
| REG | 40 | 28 | N | 2, 1BL NEED | 16.5 | 16.5 |
| REG | 40 | 34 | N | 3 | 32.3 | 32.3 |
| | | | | AVERAGE | 47.34 | 59.18 |
| | | | | STDEV | 62.28 | 65.10 |

| SUMMARY SHEET: DOINK2 | | | | | | | |
|---|---|---|---|---|---|---|---|
| CONSTANT PRESSURE: 15PSI; AIR BOLUS | | | | | | | |
| EXP # | NEEDLE | DEVICE | SPRING FORCE | SEPTUM | SAFETY | BLEBS | RATE (uL/min) | LEAKER |
| 27 | 1 | C | NONE | N | N | | 0 | Y |
| 26 | 1 | C | NONE | N | N | | 0 | Y |
| 23 | 1 | C | LOW | N | N | 2 | N/A | Y |
| 24 | 1 | C | LOW | N | N | 1 | N/A | N |
| 70 | 1 | C | LOW | N | N | 3 | 44.1 | N |
| 97 | 1 | C | LOW | N | N | | 0 | Y |
| 49 | 1 | C | LOW | N | Y | ID | 72.6 | N |
| 51 | 1 | C | LOW | N | Y | | 0 | Y |
| 25 | 1 | C | LOW | Y | N | | 28.6 | N |
| 26 | 1 | C | LOW | Y | N | | 33.18 | N |
| 62 | 1 | C | LOW | Y | N | 3 | 70 | N |
| 64 | 1 | C | LOW | Y | N | 1 | 0 | Y |
| 53 | 1 | C | LOW | Y | Y | | 0 | Y |
| 55 | 1 | C | LOW | Y | Y | | 0 | Y |
| 100 | 1 | C | LOW | Y | Y | 3 ID | 76 | N |
| 102 | 1 | C | HIGH | N | N | 2 | 0 | Y |
| 104 | 1 | C | HIGH | N | N | | 0 | Y |
| 105 | 1 | C | HIGH | N | N | 2 | 0 | Y |
| 50 | 1 | C | HIGH | N | Y | ID | 117.6 | N |
| 52 | 1 | C | HIGH | N | Y | | 103.4 | N |
| 65 | 1 | C | HIGH | N | Y | 3 | 159.3 | N |
| 105 | 1 | C | HIGH | Y | N | | 0 | Y |
| 107 | 1 | C | HIGH | Y | N | | 32.9 | N |
| 106 | 1 | C | HIGH | Y | N | 1 | 0 | Y |
| 54 | 1 | C | HIGH | Y | Y | 3 | 36.8 | N |
| 56 | 1 | C | HIGH | Y | Y | 3 | 98.4 | N |
| 58 | 1 | C | HIGH | Y | Y | | 0 | Y |

FIG. 18A

| SUMMARY SHEET: DOINK2 | | | | | | | | |
|---|---|---|---|---|---|---|---|---|
| CONSTANT PRESSURE: 15PSI; AIR BOLUS | | | | | | | | |
| EXP # | NEEDLE | DEVICE | SPRING FORCE | SEPTUM | SAFETY | BLEBS | RATE (uL/min) | LEAKER |
| 7 | 3 | C | LOW | N | N | | 628.1 | N |
| 8 | 3 | C | LOW | N | N | | 563.4 | N |
| 74 | 3 | C | LOW | N | N | | 633.5 | N |
| 41 | 3 | C | LOW | N | Y | 1 ID | 6.72 | N |
| 43 | 3 | C | LOW | N | Y | 3 | 114.8 | N |
| 56 | 3 | C | LOW | N | Y | | 475.4 | N |
| 9 | 3 | C | LOW | Y | N | | 664.8 | N |
| 10 | 3 | C | LOW | Y | N | | 679.2 | N |
| 51 | 3 | C | LOW | Y | N | | 685.8 | N |
| 45 | 3 | C | LOW | Y | Y | ID | 19.7 | N |
| 47 | 3 | C | LOW | Y | Y | ID | 34.5 | N |
| 80 | 3 | C | LOW | Y | Y | 3 | 1172.6 | N |
| 83 | 3 | C | LOW | Y | Y | | 447.8 | N |
| 67 | 3 | C | HIGH | N | N | 3 | 386.2 | N |
| 69 | 3 | C | HIGH | N | N | | 870.9 | N |
| 89 | 3 | C | HIGH | N | N | | 570.3 | N |
| 42 | 3 | C | HIGH | N | Y | SC | 486.5 | N |
| 44 | 3 | C | HIGH | N | Y | 1 | 20.3 | N |
| 73 | 3 | C | HIGH | N | Y | 3 | 1080 | N |
| 71 | 3 | C | HIGH | Y | N | 3 | 1300.3 | N |
| 72 | 3 | C | HIGH | Y | N | 3 | 754.2 | N |
| 82 | 3 | C | HIGH | Y | N | | 61.9 | N |
| 46 | 3 | C | HIGH | Y | Y | | 503.2 | N |
| 48 | 3 | C | HIGH | Y | Y | | 543.6 | N |
| 77 | 3 | C | HIGH | Y | Y | | 141.2 | N |
| 11 | 3 | C | NONE | N | N | | 1008.5 | N |
| 12 | 3 | C | NONE | N | N | | 358 | N |

FIG. 18B

| SUMMARY SHEET: DOINK2 ||||||||
|---|---|---|---|---|---|---|---|
| CONSTANT PRESSURE: 15PSI; AIR BOLUS ||||||||
| EXP # | NEEDLE | DEVICE | SPRING FORCE | SEPTUM | SAFETY | BLEBS | RATE (uL/min) | LEAKER |
| 19 | 1 | S | NONE | N | N |  | 1841.4 | N |
| 20 | 1 | S | NONE | N | N |  | 0 | Y |
| 17 | 1 | S | LOW | N | N |  | 44.1 | N |
| 10 | 1 | S | LOW | N | N |  | 0 | Y |
| 76 | 1 | S | LOW | N | N | 3 | 73.2 | N |
| 29 | 1 | S | LOW | N | Y | 3 | 88.7 | N |
| 30 | 1 | S | LOW | N | Y | 3 | 119.6 | N |
| 60 | 1 | S | LOW | N | Y |  | 0 | Y |
| 21 | 1 | S | LOW | Y | N |  | N/A | N |
| 22 | 1 | S | LOW | Y | N |  | 0 | Y |
| 31 | 1 | S | LOW | Y | N |  | 0 | Y |
| 32 | 1 | S | LOW | Y | N | 3 | 188.5 | N |
| 59 | 1 | S | LOW | Y | Y |  | 0 | Y |
| 61 | 1 | S | LOW | Y | Y | 3 | 56.1 | N |
| 91 | 1 | S | LOW | Y | Y | 1 ID | 0 | Y |
| 92 | 1 | S | LOW | Y | Y | 1 | 0 | Y |
| 93 | 1 | S | HIGH | N | N | 3 | 130.5 | N |
| 96 | 1 | S | HIGH | N | N | 3 | 67.7 | N |
| 98 | 1 | S | HIGH | N | N |  | 64.7 | N |
| 57 | 1 | S | HIGH | N | Y | 3 | 55.4 | N |
| 58 | 1 | S | HIGH | N | Y |  | 66.6 | N |
| 94 | 1 | S | HIGH | N | Y | 2 | 0 | Y |
| 85 | 1 | S | HIGH | Y | N |  | 0 | Y |
| 99 | 1 | S | HIGH | Y | N |  | 1016.1 | N |
| 101 | 1 | S | HIGH | Y | N |  | 111.7 | N |
| 83 | 1 | S | HIGH | Y | Y | 3 | 146.8 | N |
| 65 | 1 | S | HIGH | Y | Y | 3 | 0 | Y |
| 103 | 1 | S | HIGH | Y | Y |  | 197.6 | N |

FIG. 18C

| SUMMARY SHEET: DOINK2 | | | | | | | |
|---|---|---|---|---|---|---|---|
| CONSTANT PRESSURE: 15PSI; AIR BOLUS | | | | | | | |
| EXP # | NEEDLE | DEVICE | SPRING FORCE | SEPTUM | SAFETY | BLEBS | RATE (uL/min) | LEAKER |
| 3 | 3 | S | NONE | N | N | | 156.2 | N |
| 4 | 3 | S | NONE | N | N | | 628 | N |
| 1 | 3 | S | LOW | N | N | | 78.37 | N |
| 2 | 3 | S | LOW | N | N | | 614.5 | N |
| 86 | 3 | S | LOW | N | N | | 78 | N |
| 13 | 3 | S | LOW | N | Y | | 295.7 | N |
| 14 | 3 | S | LOW | N | Y | | 1032.8 | N |
| 85 | 3 | S | LOW | N | Y | 3 | 840.4 | N |
| 5 | 3 | S | LOW | Y | N | | 137.3 | N |
| 6 | 3 | S | LOW | Y | N | | 377.1 | N |
| 90 | 3 | S | LOW | Y | N | | 1016.1 | N |
| 15 | 3 | S | LOW | Y | Y | | 844 | N |
| 16 | 3 | S | LOW | Y | Y | | 577.9 | N |
| 79 | 3 | S | LOW | Y | Y | 2 ID | 8.9 | N |
| 33 | 3 | S | HIGH | N | N | | 711.4 | N |
| 34 | 3 | S | HIGH | N | N | | 1128.7 | N |
| 87 | 3 | S | HIGH | N | N | | 1003.3 | N |
| 37 | 3 | S | HIGH | N | Y | | 642.1 | N |
| 38 | 3 | S | HIGH | N | Y | | 863.5 | N |
| 75 | 3 | S | HIGH | N | Y | 2 | 68.7 | Y |
| 35 | 3 | S | HIGH | Y | N | | 935.3 | N |
| 36 | 3 | S | HIGH | Y | N | | 1235.3 | N |
| 83 | 3 | S | HIGH | Y | N | 2 SC/ID | 219 | N |
| 39 | 3 | S | HIGH | Y | Y | | 804.7 | N |
| 40 | 3 | S | HIGH | Y | Y | | 1315.7 | N |
| 78 | 3 | S | HIGH | Y | Y | 3 | 258.8 | N |

FIG. 18D

| MANIFOLD WEIGHT SUMMARY SHEET: 15OCT02 |
| --- |
| CONSTANT PRESSURE: 15PSI; 50uL AIR BOLUS |

| HEAVY MANIFOLD 3mm NEEDLE | | | | | |
| --- | --- | --- | --- | --- | --- |
| TYPE | EXP | LEAKER | BLEB TYPE | AVG RATE | IF NO LEAKS |
| HM3 | 3 | N | 3 ID | 5670 | 5670 |
| HM3 | 6 | N | 1-2 ID | 402 | 402 |
| HM3 | 12 | N | 3 ID | 1000 | 1000 |
| HM3 | 14 | N | ID-SC | 19500 | 19500 |
| | | | AVERAGE | 6643 | 6643 |
| | | | STDEV | 8889 | 8888.995219 |

| LIGHT MANIFOLD 3mm NEEDLE | | | | | |
| --- | --- | --- | --- | --- | --- |
| TYPE | EXP | LEAKER | BLEB TYPE | AVG RATE | IF NO LEAKS |
| LM3 | 7 | N | ID/SC | 31700 | 31700 |
| LM3 | 9 | N | 1 ID | 962 | 962 |
| LM3 | 10 | N | 2-3 ID | 2330 | 2330 |
| LM3 | 16 | N | SC | 64700 | 64700 |
| LM3 | 17 | N | ID/SC | 18600 | 18600 |
| LM3 | 19 | N | SC | 47300 | 47300 |
| | | | AVERAGE | 27598.7 | 27598.66667 |
| | | | STDEV | 25339.6 | 25339.55774 |

| HEAVY MANIFOLD 1mm NEEDLE | | | | | |
| --- | --- | --- | --- | --- | --- |
| HM1 | 1 | Y | 1 TINY | N/A | N/A |
| HM1 | 5 | Y | NONE | N/A | N/A |
| HM1 | 8 | Y | NONE | N/A | N/A |
| HM1 | 11 | Y | NONE | N/A | N/A |
| | | | AVERAGE | 0 | N/A |
| | | | STDEV | N/A | N/A |

| LIGHT MANIFOLD 1mm NEEDLE | | | | | |
| --- | --- | --- | --- | --- | --- |
| TYPE | EXP | LEAKER | BLEB TYPE | AVG RATE | IF NO LEAKS |
| LM1 | 2 | N | 3 ID | 3990 | 3990 |
| LM1 | 4 | N | 3 ID | 9440 | 9440 |
| LM1 | 13 | N | 3 ID | 12250 | 12250 |
| LM1 | 15 | Y | 2 SMALL ID | 0 | |
| LM1 | 18 | Y | 3 SMALL ID | 0 | |
| | | | AVERAGE | 5136 | 8560 |
| | | | STDEV | 5549.86 | 4199.726182 |

FIG. 19

DEVICE AND METHOD FOR DELIVERING OR WITHDRAWING A SUBSTANCE THROUGH THE SKIN

CROSS-REFERENCE TO RELATED APPLICATIONS

The present application is related to and claims priority to the following U.S. Provisional Patent Applications, identified by Application No. and filing date: 60/353,194, filed Feb. 4, 2002; 60/397,038, filed Jul. 22, 2002; 60/407,284, filed Sep. 3, 2002; 60/420,233, filed Oct. 23, 2002; 60/377,649 filed May 6, 2002; and 60/389,881, filed Jun. 20, 2002. The contents of each of the foregoing documents are incorporated herein by reference in their entirety.

BACKGROUND OF THE INVENTION

1. Field of the Invention

The present invention relates to a device and a method for delivering or withdrawing a substance through the skin of an animal, including humans, and in particular to a method and device for withdrawing or delivering a substance such as a drug, protein or vaccine to a subject. The invention also relates to a device for enhancing the penetration of one or more dermal-access members.

2. Related Art

The skin is made up of several layers with the upper composite layer being the epithelial layer. The outermost layer of the skin is the stratum corneum that has well known barrier properties to prevent molecules and various substances from entering the body and analytes from exiting the body. The stratum corneum is a complex structure of compacted keratinized cell remnants having a thickness of about 10–30 microns. The stratum corneum forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various substances through the skin in order to be utilized by the body. According to some methods and devices, the delivery of substances through the skin is enhanced by either increasing the permeability of the skin or increasing the force or energy used to direct the substance through the skin.

Other methods of sampling and delivering various substances through the skin include forming micropores or cuts through the stratum corneum. Numerous substances can be effectively administered by piercing the stratum corneum and delivering a substance in or below the stratum corneum. In a similar manner, some substances can be extracted from the body through cuts or pores formed in the stratum corneum. The devices for piercing the stratum corneum generally include a plurality of microneedles or blades having a length to pierce the stratum corneum. Examples of these devices are disclosed in U.S. Pat. No. 5,879,326 to Godshall et al.; U.S. Pat. No. 6,494,865 to Alchas; U.S. Pat. No. 5,997,501 to Gross et al.; U.S. Pat. No. 4,886,499 to Cirelli et al.; U.S. Pat. No. 6,183,434 to Eppstein; U.S. Pat. No. 5,250,023 to Lee et al.; International publication WO 97/48440; U.S. Pat. No. 5,527,288 to Gross et al.; and U.S. Pat. No. 3,595,231 to Pistor. Each of the foregoing documents is incorporated herein by reference in their entirety.

Some of the above-noted devices include micron-sized needles or blades and can be effective in delivering or sampling substances. However, many of these needles and blades have a length of a few microns to a few hundred microns and typically do not penetrate the skin to a uniform depth. The natural elasticity and resilience of the skin often result in the skin being deformed by the needles rather than pierced. Therefore, when a microneedle array is pressed against the skin, the outermost needles penetrate the skin while the innermost needles do not penetrate the skin or only penetrate to a depth less than the outermost needles.

Moreover, conventional devices have problems with overall height and ease of use. As a result, the prior methods and devices for the sampling and administering of substances have exhibited limited success. Accordingly, a continuing need exists in the industry for an improved device for the sampling and administering of various substances to the body.

SUMMARY OF THE INVENTION

These and other objects are accomplished by a method and device according to the present invention.

A device for delivering or withdrawing a substance, typically a fluid, below the stratum corneum is provided. A body of the device includes a top face, a bottom face spaced from the top face, and a side edge. Typically, a channel is defined within the body. The bottom face includes a first surface area and a second surface area adjacent to and recessed from the first surface area. The bottom face further includes at least one raised protrusion disposed on the second surface area. At least one dermal-access member is provided in each raised protrusion and is in fluid communication with the channel to deliver or withdraw the substance.

Similarly, a method of delivering or withdrawing a substance through at least one layer of the skin of a subject is provided. The method includes the steps of: providing a device having a body having a top face, a bottom face spaced from the top face, and a side edge, the body defining a channel within the body, and at least one dermal-access member coupled to and extending outwardly from said bottom face and being in fluid communication with the channel, wherein the bottom face includes a first surface area and a second surface area adjacent to and recessed from the first surface area, the bottom face further including at least one raised protrusion disposed on the second surface area, at least one dermal-access member installed in at least one raised protrusion; positioning the dermal-access member on a target site of the skin of the subject; applying a pressure against the device sufficient for at least one dermal-access member to penetrate the skin and for the first surface area to contact the skin; and delivering a substance to or withdrawing a substance from the target side of the subject.

In particular, a method and apparatus for delivering a substance, such as a drug, protein or vaccine, into or below the stratum corneum of the skin to a sufficient depth where the substance can be absorbed and utilized by the body is provided.

The device and method according to an embodiment of the present invention are suitable for use in administering various substances, including pharmaceutical and bioactive agents, to a subject, preferably a mammal, and particularly to a human patient. Such substances have biological activity and can be delivered through the body membranes and surfaces, and particularly the skin. Examples include, but are not limited to antibiotics, antiviral agents, analgesics, anesthetics, anorexics, antiarthritics, antidepressants, antihistamines, anti-inflammatory agents, antineoplastic agents, vaccines, including DNA vaccines, and the like. Additional substances that can be delivered to a subject include proteins, peptides and fragments thereof. The proteins and peptides can be naturally occurring, synthesized or produced by recombination.

The device and method may also be used for withdrawing a substance or monitoring the level of a substance in the body. Examples of substances that can be monitored or withdrawn include blood, interstitial fluid or plasma. The withdrawn substances may then be analyzed for various components or properties.

The dermal-access member according to the invention is any member which penetrates the skin of a subject to the desired targeted depth within a predetermined space without passing through it. In most cases, the device will penetrate the skin to a depth of about 0.3–3 mm. Generally, the device is utilized for intradermal administration, for example, with a configuration sufficient to penetrate at a depth of about 1.0–1.7 mm. However, the device can also be used to deliver a substance to a depth of about 0.3 mm or less and at subcutaneous depths of 1.7 mm–3.0 mm depths or greater.

The dermal-access members may comprise conventional injection needles, catheters or microneedles of all known types, employed singularly or in multiple member arrays. The terms "dermal-access member" and "dermal-access members" as used herein are intended to encompass all such needle-like structures. The dermal-access members can include structures smaller than about 28 gauge, typically about 29–50 gauge when such structures are cylindrical in nature. Generally, the dermal access members will be about 30–36 gauge. Non-cylindrical structures encompassed by the term dermal-access member would therefore be of comparable diameter and include pyramidal, rectangular, octagonal, wedged, triangular, hexagonal, cylindrical, tapered and other geometrical shapes and arrangements. For example, the dermal-access members can be microtubes, lancets and the like. Any suitable delivery mechanism can be provided for delivering the substance to the penetrated skin.

By varying the targeted depth of delivery of substances by the dermal-access members, pharmacokinetic and pharmacodynamic (PK/PD) behavior of the drug or substance can be tailored to the desired clinical application most appropriate for a particular patient's condition. The targeted depth of delivery of substances by the dermal-access members may be controlled manually by the practitioner, with or without the assistance of an indicator mechanism to indicate when the desired depth is reached. Preferably however, the device has structural mechanisms for controlling skin penetration to the desired depth. This is most typically accomplished by means of a widened area or hub associated with the shaft of the dermal-access member that may take the form of a backing structure or platform to which the dermal-access members are attached. The length of dermal-access members are easily varied during the fabrication process and are routinely produced at less than 3 mm in length. The dermal-access members are typically sharp and of a very small gauge, to further reduce pain and other sensation when the dermal-access members are seated in the patient. The invention may include a single-lumen dermal-access member or multiple dermal-access members assembled or fabricated in linear arrays or two- or three-dimensional arrays to increase the rate of delivery or the amount of substance delivered in a given period of time. Dermal-access members may be incorporated into a variety of devices such as holders and housings that may also serve to limit the depth of penetration. The dermal-access members of the invention may also incorporate or be in fluid communication with reservoirs to contain the substance prior to delivery or pumps or other means for delivering the substance into the patient under pressure. Alternatively, the dermal-access members may be linked externally to such additional components.

The device may include a luer type or other connection port for connection to a fluid delivery system such as a syringe, a pump, or a pen. In such an embodiment, the device may use a length of tubing for feeding a low dead volume body through an opening in the body.

Any suitable mechanism for delivering a fluid to the dermal-access members can be used. For example, a luer connection can be secured directly to the device for delivering a fluid from tubing or directly from a syringe secured to the luer connection. Furthermore, the device or portions of the device can be incorporated into an applicator that applies the device to a patient in a consistent manner, for example, at a consistent pressure, velocity and dose.

As an option, a removable shield can protect the device and particularly, the dermal-access members until use.

In addition to being a useful device for penetrating skin at an exact depth and for supplying an exact amount of fluid, the device is useful in enabling the placement of multiple dermal-access members simultaneously in a patient. This type of application is useful in both device and drug testing applications.

When the device is used to deliver substances to the intradermal space of a patient, the delivery of the substance typically results in one or more blebs left in the skin. As used herein, bleb refers to any site of deposition of a substance below the stratum corneum of the skin, generally in the intradermal space. Typically, the bleb extends laterally from the point of administration and distends upward. The bleb diameter and height are functions of instilled volume and rate of delivery and other factors. Secondary physiology effects, such as irritation or histamine release, can also alter bleb dimensions. Bleb duration can be a function of uptake distribution and clearance of the instilled components, both individually and in combination. Multiple blebs can be either overlapping or non-overlapping. Non-overlapping blebs allow for increased area of administration, but may contribute to imbalanced flow to individual points of administration within a system. Overlapping blebs may contribute to increase distension of tissue space, and result in better equilibrium of infusion pressure, but limits the benefits of increased fluid volume.

The device is constructed for penetrating selected layers of the dermis of a subject to a desired depth. The desired depth of penetration is usually determined by the substance being delivered or withdrawn and the target site. In this manner, a substance can be delivered, absorbed and utilized by the body substantially without pain or discomfort to the subject.

The advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings.

FIG. 17 is a table of results for an experiment indicating the effectiveness of one aspect of the present invention.

FIGS. 18A–D are tables of results for an experiment indicating the effectiveness of one aspect of the present invention.

FIG. 19 is a table of results for an experiment indicating the effectiveness of one aspect of the present invention.

DETAILED DESCRIPTION OF AN EXEMPLARY EMBODIMENT OF THE PRESENT INVENTION

A preferred embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention.

Figure 1:
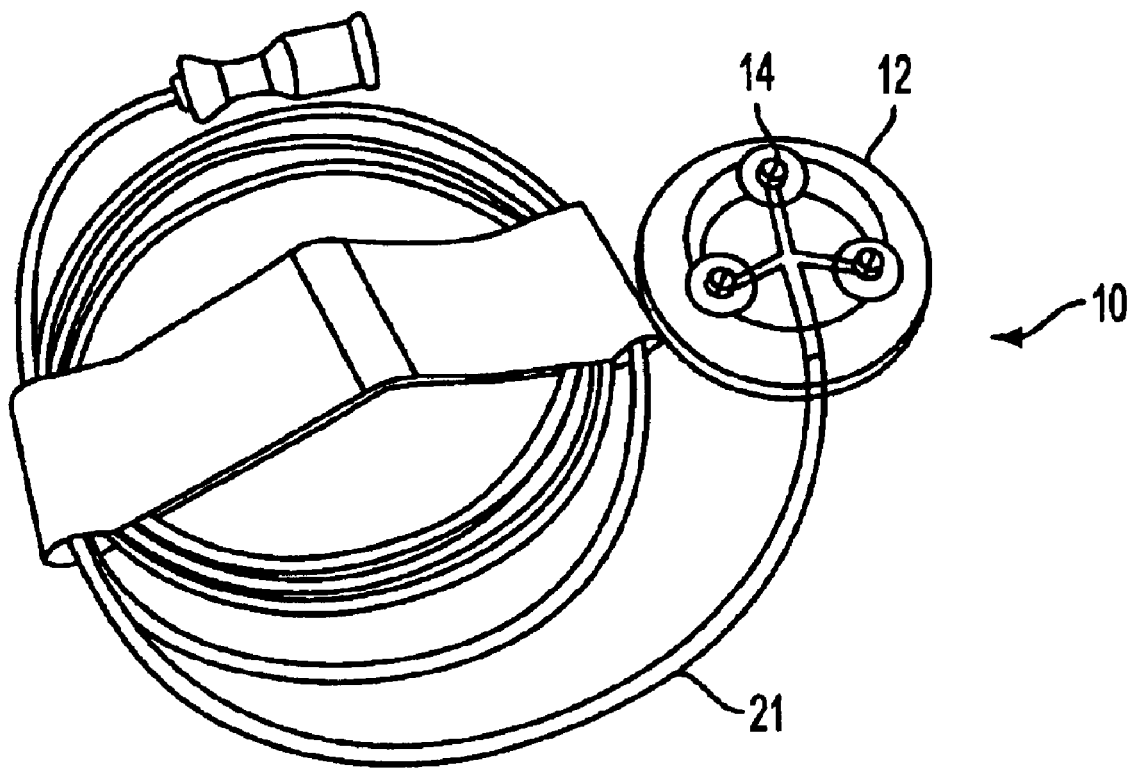
FIG. 1 is a perspective view of the device in accordance with an embodiment of the invention for sampling or delivering a substance through the skin of a subject.
Figure 2:
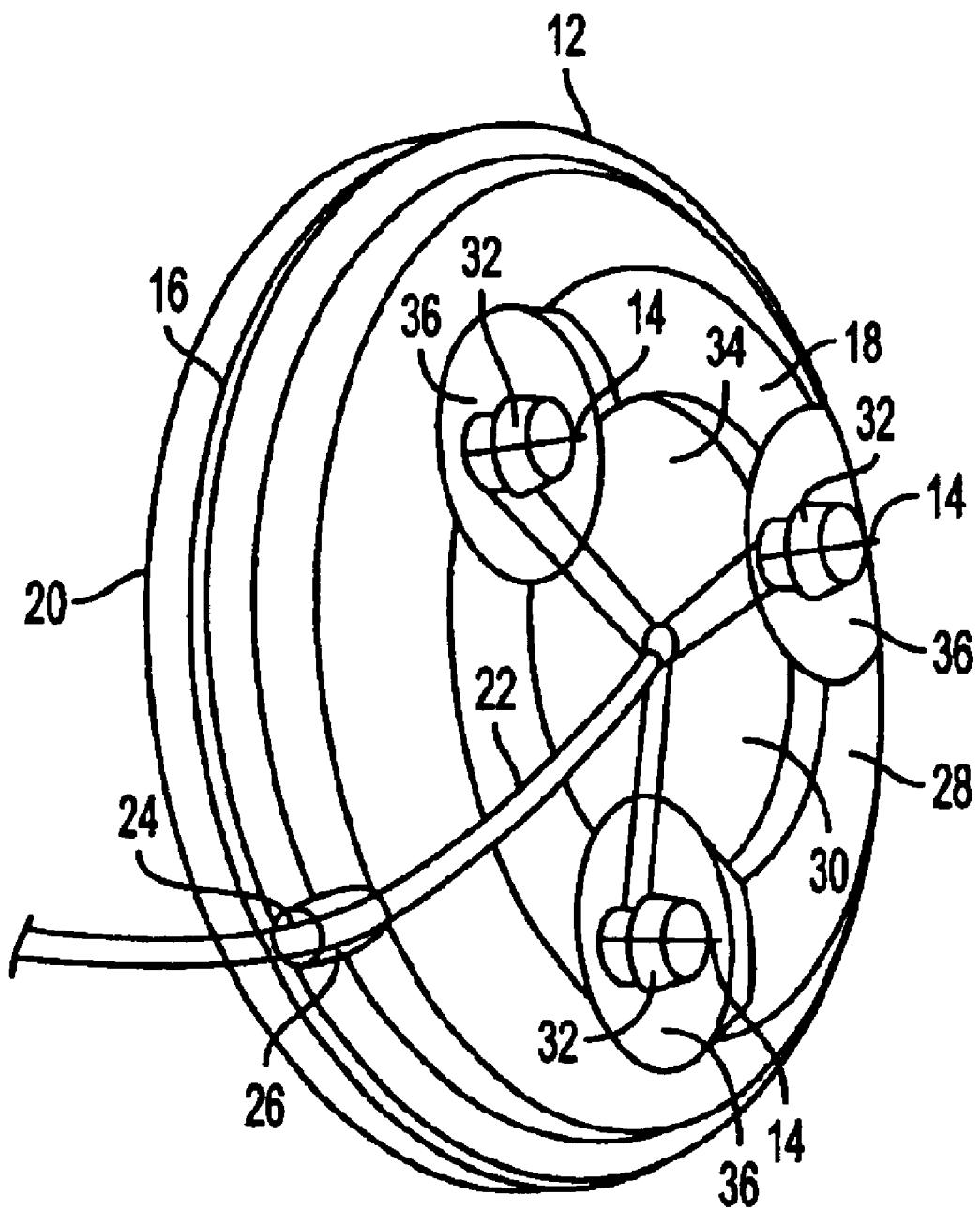
FIG. 2 is an enlarged view of the bottom face of the device shown in FIG. 1.

Referring to the drawings, particularly FIGS. 1 and 2, a first, exemplary embodiment of the invention is now described. As described herein and shown in all of the figures, analogous or identical features are indicated by the same reference number.

A device 10 according to the present invention has a body 12 and dermal-access members 14. The device 10 optionally includes tubing 21 for delivering fluid to or removing fluid from the body 12 of the device.

The body 12 optionally has a low profile to lie flat against the skin of a subject. The low profile of the body 12 provides for ease of attachment to the skin and less obstruction to the subject. The low profile can be achieved by reducing the thickness of the body 12. In the embodiment shown, the body 12 has a substantially circular disk shape, although in alternative embodiments, the body 12 can have a non-circular or other more angular shape or be slightly arcuate.

As an example, the diameter of the circular body 12 is preferably about 1–10 cm or less, although other sizes and shapes can be used. Embodiments can be manufactured with diameters of 5 mm or smaller.

The body 12, as shown in FIG. 2, has a circular outer side edge 16, a top face 20 and a bottom face 18. The outer side edge 16 preferably has a rounded surface. The rounded surface helps control the pressure distribution on the device 10 and subject during application. Tapering and contouring help tension the skin at a controlled rate to allow the dermal-access members 14 to penetrate the skin with less force than would otherwise be required.

One or more fluid channels 22 are provided in the body 12. The fluid channel 22 has an open inlet end 24. A coupling member 26 is optionally provided for coupling a fluid delivery mechanism to the body 12 at the open inlet end 24. Alternatively, no coupling member is provided and the fluid delivery mechanism is secured directly to the body 12. An axis of the fluid channel 22 optionally extends substantially parallel to the plane of the body 12. In this manner, the body 12 maintains a substantially flat, low profile configuration. Of course, other arrangements of the coupling member 26 and the fluid channel 22 are possible.

In the embodiment shown in FIGS. 1 and 2, the bottom face 18 of the body 12 has first 28 and second 30 surface areas. The first surface area 28 is raised from the body 12 with respect to the second surface area 30. Thus, the second surface area 30 defines a recessed area on the bottom face 18 relative to the first surface area 28.

Raised protrusions 32 are provided in the recessed second surface area 30. As an exemplary embodiment, each protrusion 32 can be formed as a raised conical protrusion. As an alternative, other shapes such as cylindrical shapes may be used. Optionally, a raised conical protrusion 32 can have a flat upper surface to form a conical plateau or lower frustum of a cone. As an alternative, other upper surface shapes and contours may be used.

As shown in FIGS. 1 and 2, the recessed second surface area 30 comprises a central recessed area 34, preferably located in the center of the bottom face 18, and substantially circular recessed areas 36 surrounding each of the protrusions 32. In one embodiment, the recessed second surface area 30, including the central recess 34 and other recesses 36, are recessed at about 1 mm relative to the surrounding first surface area 28, although the depth of the recess can vary from about 0.1 mm and less to about 10 mm. As an example, the recesses 36 surrounding each of the protrusions 32 are about 5 mm in diameter, although the diameter of the recess can vary, for example to about 50 mm. The recesses 36 typically provide an area for the bleb to form. The diameter and arrangement of the recesses 36 and corresponding protrusions 32 can depend on the desired delivery characteristics. Other suitable recess arrangements can be designed depending on the bleb characteristics desired, the volume of substance to be delivered, the rate of delivery of the substance, and other factors. As one option, the diameter of the recess 36 surrounding each of the protrusions 32 can be calculated by one of ordinary skill in the art based on the volume and rate of the fluid administered.

As shown in FIG. 2, the three protrusions 32 and corresponding recessed areas 36 are spaced at 120° relative to one another on the bottom face 18, although arrangements can vary. Some of the alternative arrangement are shown in further embodiments and discussed herein. In the embodiment shown, the center of each protrusion 32 is equally spaced at a distance of about 7.5 mm from the center of the bottom face 18, although, as discussed above, other arrangements can be used depending on the desired delivery characteristics. As an example, the protrusions 32 are about 2 mm in diameter at the top of the protrusion 32 and may have an approximately 10° draft from top to base. The draft of the protrusions 32 can range, for example, from 0° to 60°. The shape and sizes of the protrusions 32 can vary, although typically, the top of the protrusion will range from 0.5 mm or even smaller to about 10 mm in diameter. The diameter and shape of the protrusions 32 can be based on, for example, dermal-access member seating requirements.

In the embodiment shown, one dermal-access member 14 is provided in each conical protrusion 32, although multiple dermal-access members 14 can be provided in each conical protrusion. Thus, in the embodiment shown in FIGS. 1 and 2, three dermal-access members 14 are provided.

The upper surface of the raised conical protrusion may be slightly elevated relative to the first surface area 28, flush with the first surface area 28, or slightly recessed relative to the first surface area 28. It is understood that the relative heights of the respective surfaces may vary depending on desired bleb formation, skin tensioning characteristics, and dermal-access member seating requirements. As an exemplary embodiment, the first surface area 28 will be slightly lower than the top of the protrusions, for example 0.25 mm shorter.

Outside of the first surface area 28, the device 10 chamfers to the outer edge 16 to prevent or reduce edge effect, defined as pressure applied to the outer edge of the device that may impede performance of the device 10 or cause the subject discomfort.

In the embodiment shown, each dermal-access member extends about 1 mm from the top of the protrusion 32 with about 0.5 mm to about 2 cm of the dermal-access member remaining within the protrusion 32. In an exemplary embodiment, the device uses hollow dermal-access members 14. The dermal-access member tips can be beveled, for example, at a single bevel angle of approximately 15–35°, preferably 28°.

As shown in FIG. 2, the fluid channel 22 extends between the inlet 24 and the protrusions 32 for supplying a substance to the dermal-access members 14 or for directing a substance withdrawn from a subject to a suitable collection container. In one embodiment, the top face 20 of the body 12 defines the channel 22. Optionally, the channel 22 is open with respect to the top face 20. The channel 22 extends from the opening inlet 24 to each of the dermal-access members 14. In the embodiment shown, the channel 22 includes a central channel 23 from the inlet 24 to the center of the top face 20 and extends from the center outwardly to each protrusion 32.

The device 10 can also include a cover portion (not shown in FIGS. 1 and 2) for covering the channel 22. The cover portion may be glued onto the body 17 with UV cure adhesive or other attachment mechanism.

In the embodiment shown, the tubing 21 delivers fluid to the channel 22. The tubing 21 is secured to the inlet end 24 of the body 12. The tubing 21 may be glued to the coupling member 26. Optionally, the tubing 21 includes 16 gauge catheter tubing with a luer fitting (not shown). The other end of the tubing can be connected to a supply or receiving device. The supply device may be a syringe (not shown), a unit dose delivery device (not shown), or a suitable metering pump or infusion device (not shown) for delivering a substance to device 10 at a controlled rate. This method can also be used to withdraw a substance from a subject.

In an exemplary embodiment, the channel 22 is smaller than the tubing 21 feeding the channel 22, but significantly larger than the exit diameters of the dermal-access members 14 so as not to result in unnecessary high pressures. The tubing should not be the limiting factor in the flow of substance through the device. Optionally, the size and configuration of the dermal-access member and arrangement of recesses are the primary factors in controlling substance delivery. The body 12 of the delivery device is preferably designed to deliver fluids in the range of about 2–5 psi up to about 200 psi, for example, 50–75 psi. The body 12 can also be designed to deliver at higher and lower pressures. The body and all fitting and components of the device should be rigid enough to withstand pressures on the device without deflection or loss of liquid sealing.

The device 10 may be taped with tape 38, or otherwise secured, onto a subject during application. Alternatively, the device can be manually held in place without any other securing mechanism. The device 10 can also be designed and/or manufactured with tape or other suitable securing mechanism, such as an adhesive, as part of the device 10. Optionally, the device can be installed or incorporated into an applicator device for mechanically applying the device to a user.

Figure 3:
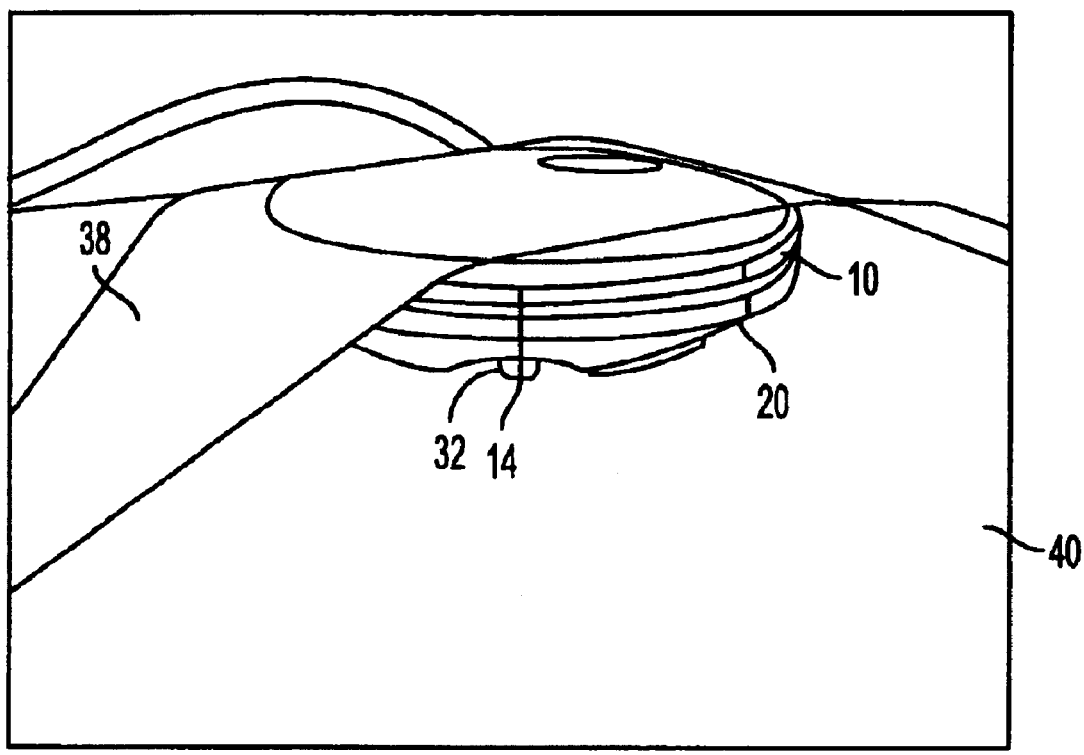
FIG. 3 is a side elevational view showing the device of FIG. 1 interfacing with the skin of a subject.
Figure 4:
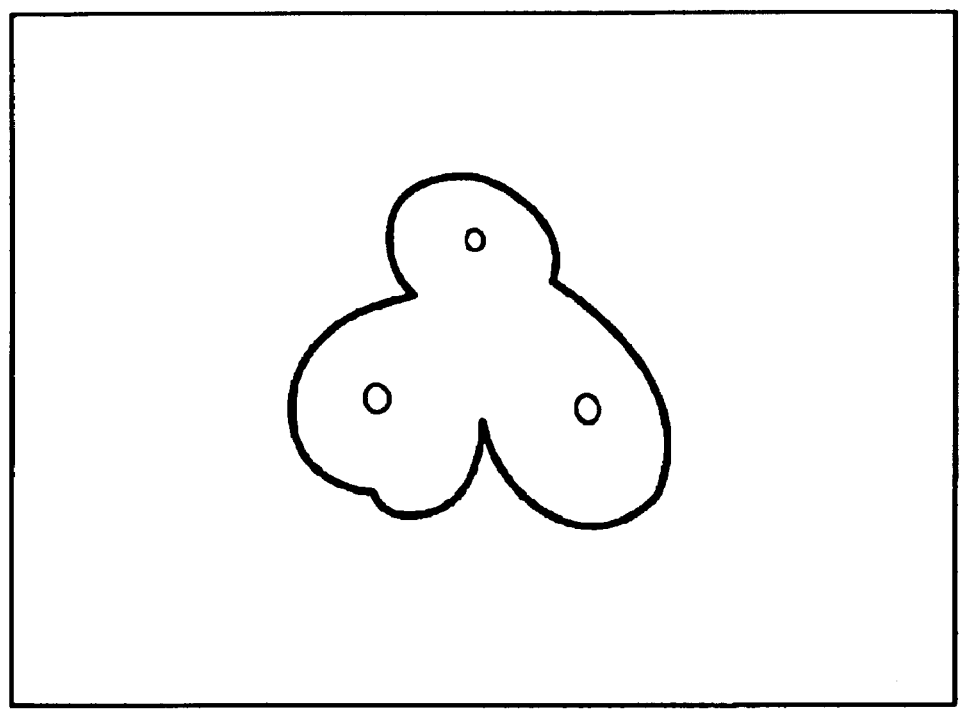
FIG. 4 is a view of the bleb pattern formed after application of the device in FIG. 3.

FIG. 3 illustrates the delivery device of FIGS. 1 and 2 in use, taped to the subject 40. FIG. 4 shows the bleb pattern resulting from the application shown in FIG. 3. As shown in FIG. 4, application of this embodiment of the delivery device results in a three-bleb pattern.

Figure 5:
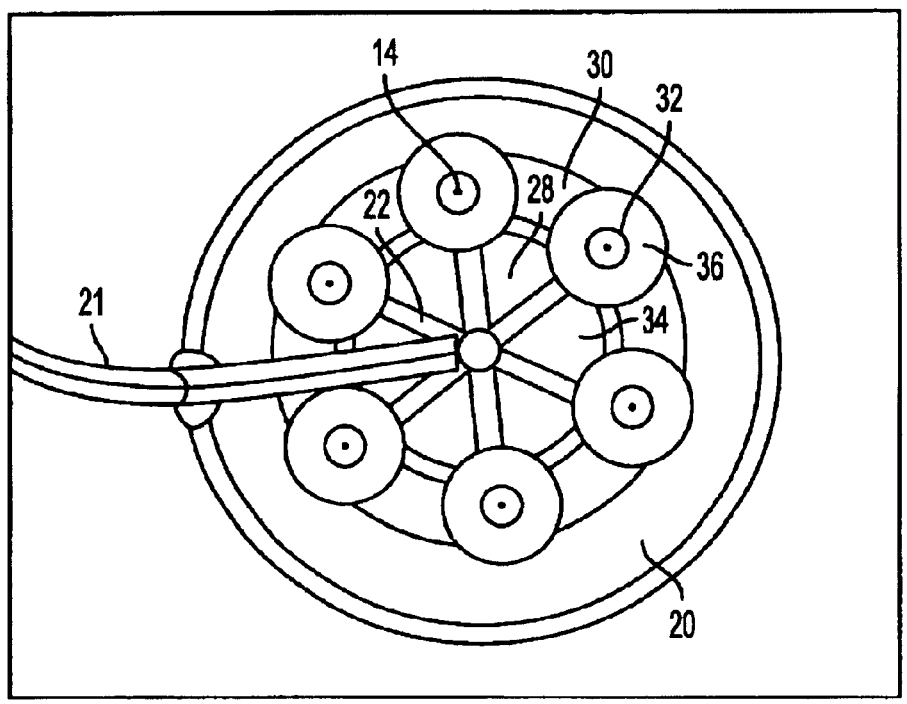
FIG. 5 is a view of the bottom face of a further embodiment of the device.

FIG. 5 shows another embodiment of the device. This embodiment is similar to the previous embodiment. However, instead of the three member array shown in FIGS. 1–3, the device shown in FIG. 5 includes a six member array with six protrusions 32 and six dermal-access members 14.

Figure 6:
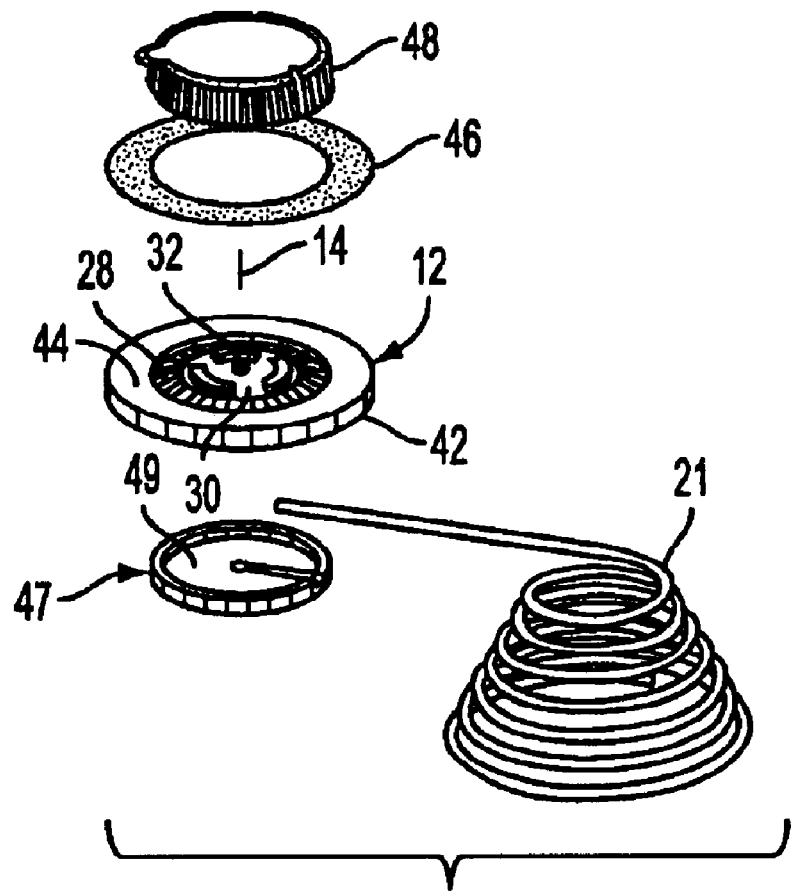
FIG. 6 is an exploded perspective view of an alternate embodiment of the device.

FIG. 6 shows a further embodiment of the device. Other than the differences discussed below and illustrated in the Figures, this embodiment is similar to the other embodiments. This embodiment is a single member delivery device 10 with one protrusion 32 and one dermal-access member 14. The device 10 shown in FIG. 6 also differs from the devices of FIGS. 1–5 in that a flange 44 is provided for application of adhesive.

In the example shown in FIG. 6, the body 12 is optionally about 3.8 cm or less in diameter, for example, about 1.2 cm. On the center of the bottom face 18 in the recessed second area 30, the protrusion 32 is formed. In this embodiment, the central recessed area and the circular recessed area are the same area 30 because only one centrally located protrusion 32 is provided. One dermal-access member is installed in the protrusion 32.

A chamfer 42 extends to the edge of the device. The chamfer 42 helps ensure that the proper pressure is applied to the dermal-access member 14 and prevents any adverse effect of the edge from the device during delivery.

In the embodiment shown, the flange 44 surrounds the edge 45 for application of an adhesive ring 46. The flange 44 can, for example, extend about 1 cm beyond the edge of the device. The flange can be rigid or flexible and can be designed to extend as far as necessary beyond the edge of the body 12, depending on the necessary level of securement and its placement on the subject. The flange 44 should be slightly recessed relative to the first areas 28 to compensate for the thickness of the adhesive 46, and to minimize or eliminate interference with the delivery area. For example, the flange can be recessed 1 mm although the amount the flange 44 is recessed can vary. Generally, the adhesive 46 should be located at a distance from the delivery site, preferably, as far away as is practical, so as not to interfere with delivery characteristics.

The adhesive 46 is preferably a pressure sensitive adhesive capable of attaching the device 10 to the surface of the skin of a subject and is preferably applied directly to the flange 44. The adhesive 46 can be a double-faced adhesive foam tape having one face bonded to the flange 44. The device 10 is preferably packaged with a release sheet covering the adhesive 46 that can be removed immediately before use. As an alternative, any suitable means for maintaining biological interface of the device with a subject may be used.

The flange 44 and adhesion arrangement 46 can also be provided in the other embodiments.

A cover portion 47 is provided to seal the fluid channel 22. The cover portion 47 has an inside face and an outside face (not shown). Preferably, the cover portion 47 is circular with a recess 49 on the inside face that accommodates the raised area (not shown in FIGS. 6 and 7) on the top face of the body 12. As an example, the cover portion 47 can have a diameter corresponding to the body 12 of the device 10. The recess 49 can be deep enough to accommodate the corresponding raised area of the body. The recess 49 and raised area of the body act as a locating aid for placement of the cover portion. The inside of the cover portion 47 can also define a groove (not shown) which mates with a corresponding rib (not shown in FIGS. 6 and 7) on the top face of the body 12. Preferably, the groove is more shallow than the rib to prevent any possible wicking of adhesive. The rib on the top face allows for location and alignment of the cover portion 47. The cover portion 47 and raised area can also be designed to account for adhesive used to adhere the cover portion to the body 12. The cover portion 47 defines a mating half of the fluid channel 22 to allow for obstruction free insertion of the tubing 21. The cover portion 47 can be of sufficient thickness to help reduce deflection of the cover portion when pressurized. As an option, the cover portion 47 should not be set on the flange 44, but instead, on the body, which, as discussed above, is of a rigid design to prevent deflection.

Shield 48 can be provided for protecting the dermal-access member 14 before use. As shown in FIG. 6, the shield 48 can have a tabbed lid with three slots to allow it to be press fitted inside the diameter of the adhesive ring. Alternatively, the shield 48 can have any suitable design which protects the dermal-access member prior to use.

Figure 7:
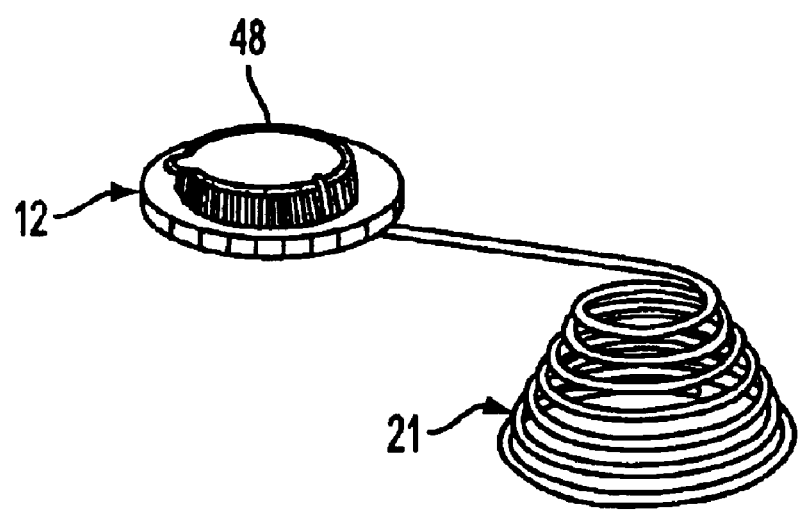
FIG. 7 is a perspective view of the embodiment of the device shown in FIG. 6.

FIG. 7 shows the assembled device from FIG. 6.

Figure 8:
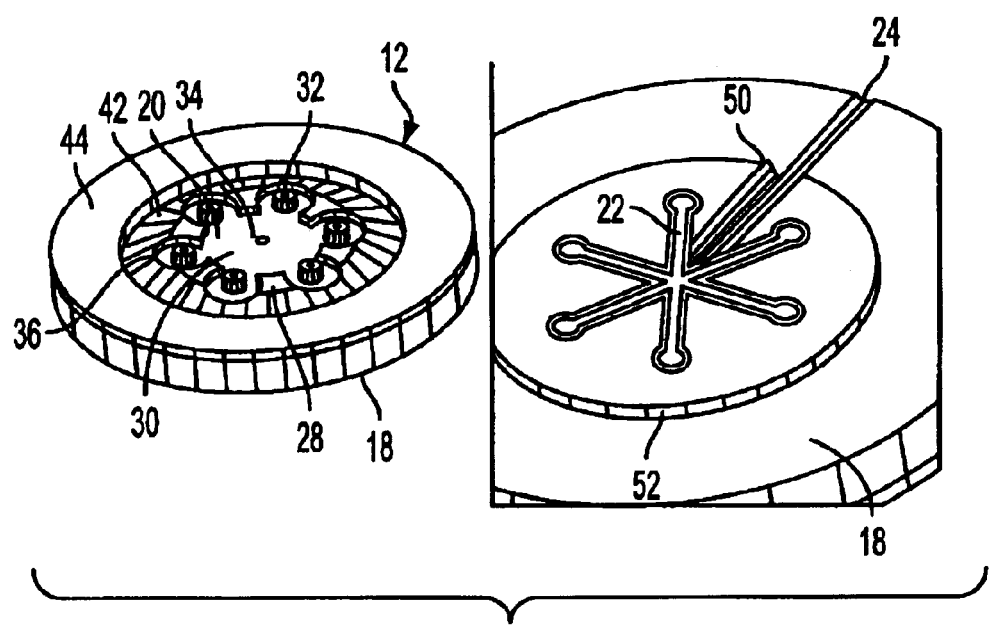
FIG. 8 shows perspective views of the top face and the bottom face of another embodiment of the device.

FIG. 8 shows another embodiment of the invention. This embodiment is similar to the embodiment shown in FIG. 6. The bottom face 18 of the body has a six member array of six protrusions 32 and six dermal-access members 14. The bottom face 18 has a raised first surface area 28 and a recessed second surface area 30. The protrusions 32 are provided on the second surface area 30. The bottom face 18 also has a chamfered surface 42 extending from the first surface 28 to the edge 43. A flange 44 is provided for application of adhesive.

FIG. 8 also shows the top face 20 of the body 12. The top face 20 of the body 12 defines a channel 22 for insertion of tubing 21 for delivery of the fluid. This feature may be present in the other embodiments, although not clearly shown in previous figures. The channel 22 may extend from the edge of the main body 12 at inlet port 24 to the center of the top face 20 of the body 12 and is in fluid communication with the dermal-access member 14. In the exemplary embodiment, the tubing extends into the body to a narrowing stop in the channel. However, the device can be designed with the tubing extending only to the edge of the device or all the way through the channel to the dermal-access members. The channel 22 can be, for example, about 1 mm in diameter, although the channel can be modified depending on the desired delivery characteristics, including delivery rate and volume. The channel 22 can narrow as necessary to reduce any dead space inside the device but outside the tubing. For example, the channel can be 0.5 mm in diameter or less. Dead space results in wasted substance remaining in the device and not delivered to the subject and/or requires more pressure than would otherwise be necessary to deliver the substance to the subject. The top face 20 of the body 12 also has a raised area 52 on the center of the top face 20. The raised area 52 has a wall or rib 50 surrounding the fluid channel 22 to enhance sealing of the channel 22 and to prevent any adhesive from wicking into the fluid channel during assembly. As an example, the rib 50 can be about 0.5 mm in height. A cover portion (not shown) can be provided to enclose the open channel.

Figure 9:
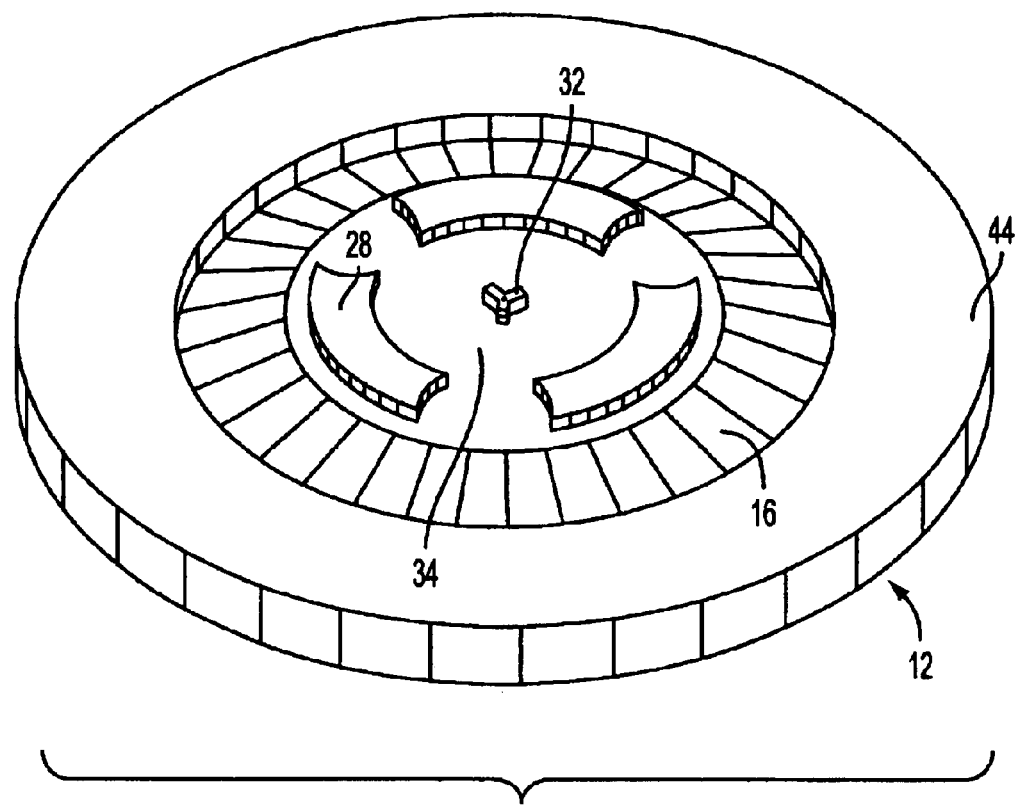
FIG. 9 is an enlarged perspective view of the bottom face of another embodiment of the device.

FIG. 9 is an enlarged perspective view of the bottom face of another embodiment. The bottom face 18 of the body 12 shown in the embodiment of FIG. 9 is similar to the device shown in FIG. 6. The embodiment of FIG. 9 is a single member array with a single protrusion 32. Instead of being a conical protrusion, the protrusion 32 has arms extending at 120° from one another. The device of FIG. 9 has a three portion first surface area 28 and an edge 16 that chamfers to the flange 44.

As shown by the alternate protrusion shown in FIG. 9, the protrusions of any of the embodiments can be any suitable shape or arrangement to achieve optimal results. For example, the protrusions can have cylindrical, pyramidal, or other geometrical configurations. As a further alternative, the protrusions can be arranged as a type of sleeve supporting the dermal-access member which retracts upon application. The protrusions can be arranged on a flexible hinge region, such as a flexible membrane or temperature sensitive polymer, which also retracts in a longitudinal direction upon application. In addition, the upper surface of the protrusion can be flat, concave or convex. Alternatively, the dermal-access member can be supported directly on the second surface area without any protrusion or with a protrusion that provides minimal support.

Figure 10:
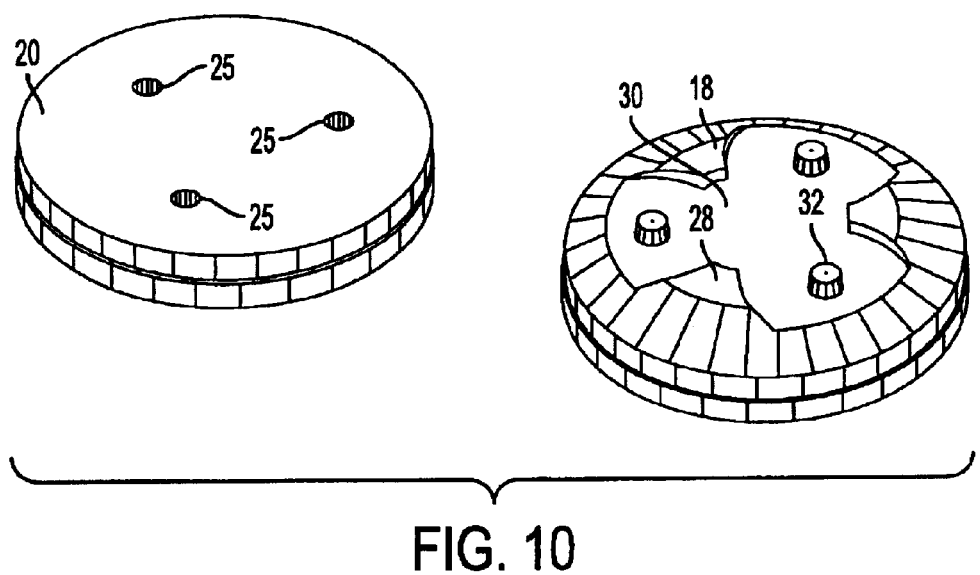
FIG. 10 is a perspective view of the top and bottom faces of another embodiment of the device.

FIG. 10 is a perspective view of the top 20 and bottom 18 faces of another embodiment of the present invention. The device shown in FIG. 10 is a three member array with three protrusions. Instead of having a longitudinal channel defined on the top face of the body, which extends from the edge of the device to a dermal-access member, the embodiment of FIG. 10 has individual channels 25 in fluid communication with the dermal-access members (not shown in FIG. 10). In the embodiment shown, the individual channels 25 extend perpendicularly directly from the top face 20 to the protrusions 32 and the dermal-access members. Any suitable mechanism, such as a syringe or pump, can be used to deliver or extract fluid from the individual channels 25. Individual channels 22 can be useful in delivering different fluids to a subject or delivering fluids at different pressures. For example, as shown in FIG. 10, three separate delivery means could deliver fluid to the device.

Figure 11:
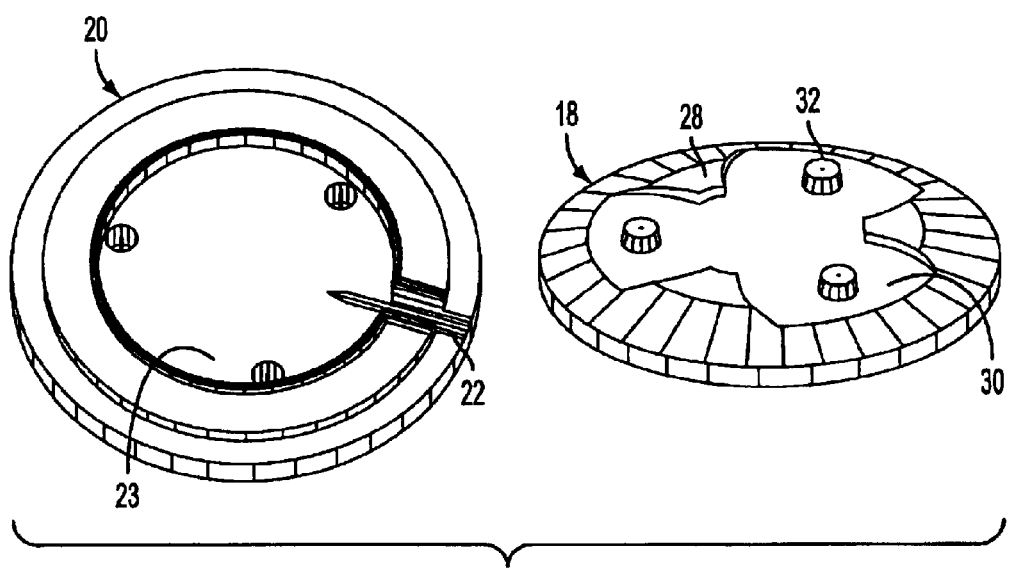
FIG. 11 is a perspective view of the top and bottom faces of a further embodiment of the device.

FIG. 11 is a perspective view of the top 20 and bottom faces 18 of another embodiment of the present invention. The device shown in FIG. 11 is a three point array with three protrusions 32. Instead of having a longitudinal channel defined on the top face of the body which extends from the edge of the device to a dermal-access member, the embodiment of FIG. 11 has a reservoir 23 defined on the top face 20. Fluid is introduced from the relatively shorter longitudinal channel into the reservoir 32. The fluid is communicated from the reservoir 32 to the dermal-access member (not shown in FIG. 11).

FIGS. 12–15 show still further embodiments of the device. Generally, the embodiments shown in FIGS. 12–15 are smaller than those shown in FIGS. 1–3 and 5–11.

Figure 12:
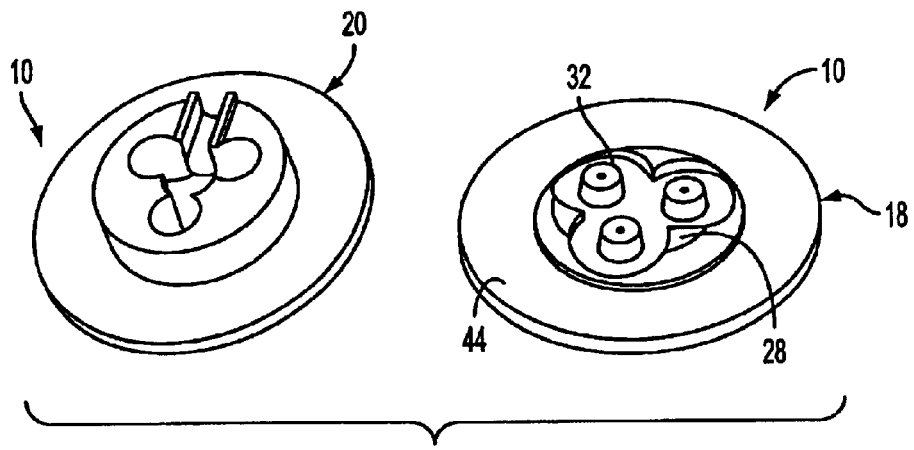
FIG. 12 is a perspective view of the top and bottom faces of an additional embodiment of the device.
Figure 13:
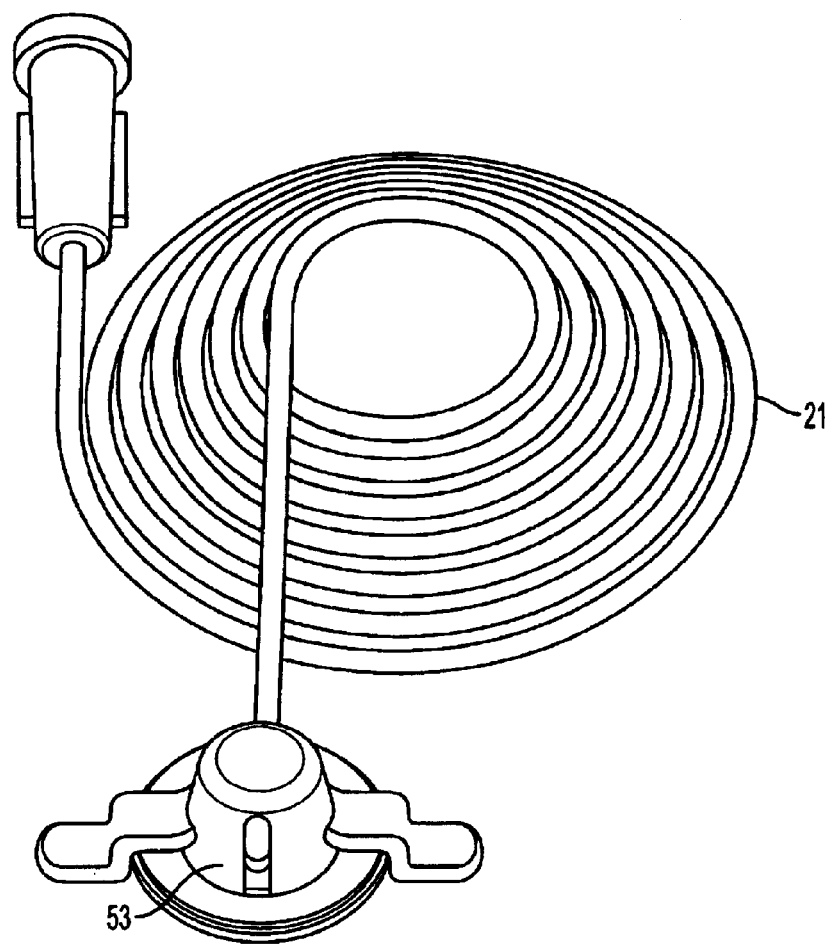
FIG. 13 is a perspective view of the device of FIG. 12 with additional assembled components.

The device 10 shown in FIGS. 12 and 13 is a three member array with a bottom face 18 having three protrusions 32 and a flange 44. As shown in FIG. 12, the dermal-access members have not yet been installed. The top face 20 has a raised portion 54 at least in part defining flow paths to the protrusions and configured to receive a cap assembly 53. The cap assembly 53 and tubing 21 for delivering the fluid to the patient during use is shown in FIG. 13.

As an example, the device 10 shown in FIGS. 12 and 13 has a thickness of about 5 mm and a diameter of about 18 mm with the flange 44. The body chamfers at 45° to the flange 44. The protrusions 32 extend slightly above the raised first surface area 28, for example about 0.2–0.3 mm above the first surface area 28. The top face of each of the protrusions 32 is about 2 mm in diameter. The protrusions 32 are spaced equally around the center of the top face 20, and the distance from the center of a protrusion 32 to the center of the device 10 is 2.5 mm.

Figure 14:
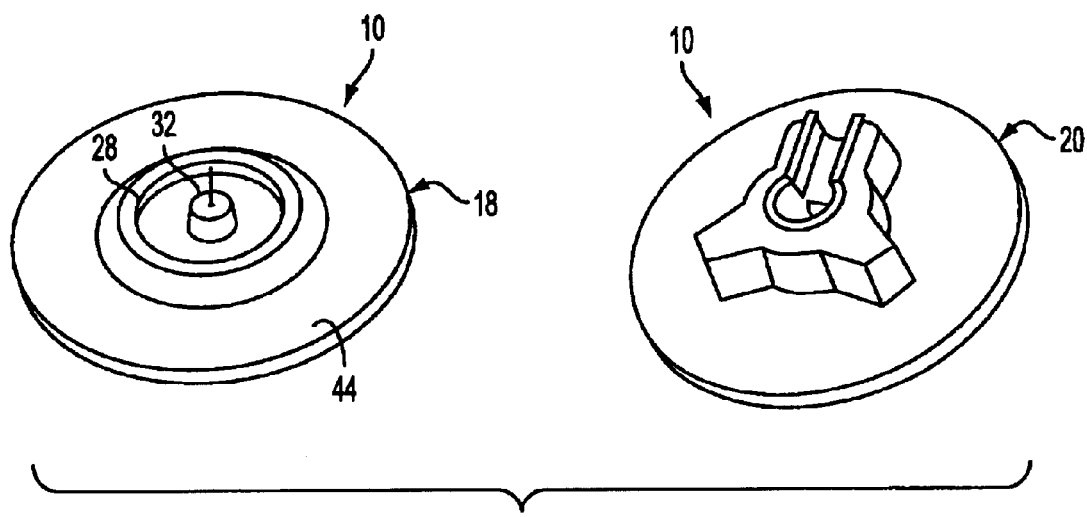
FIG. 14 is a perspective view of the top and bottom faces of a further embodiment of the device.

The device 10 shown in FIG. 14 is a single dermal-access member device with a bottom face 18 having a single dermal-access member installed in the protrusion 32. The top face 20 has a raised portion 54 at least in part defining a flow path to the protrusion and configured to receive a cap assembly (not shown).

By way of example, the device 10 shown in FIG. 14 is about 5 mm thick and has a diameter of about 18 mm with the flange 44. The protrusion 32 extends slightly above the raised first surface area 28, for example about 0.2–0.3 mm above the first surface area 28. The top face of the protrusion 32 is about 2 mm in diameter.

Figure 15:
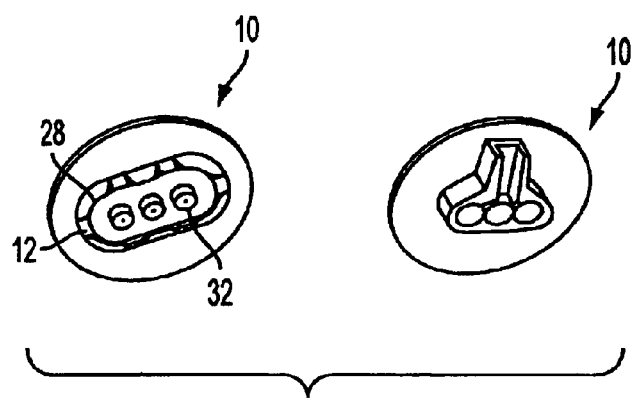
FIG. 15 is a perspective view of the top and bottom faces of a further embodiment of the device.

The device 10 shown in FIG. 15 is a three dermal-access member linear array with a bottom face 18 having three protrusions 32. The top face 20 has a raised portion 54 at least in part defining flow paths to the protrusions and configured to receive cap assembly (not shown). The dermal-access members are not yet installed in FIG. 15. Both the device 10 and body 12 are elliptical.

By way of example, the elliptical embodiment of the device 10 shown in FIG. 15 is about 5 mm thick and has length of about 19.5 mm and a width of about 23 mm. The body 12 has a length of about 15 mm and a width of about 9 mm. The protrusions 32 extend slightly above the raised first surface area 28, for example about 0.2–0.3 mm above the first surface area 28. The top faces of the protrusions 32 are about 2 mm in diameter, and the center of a protrusion is spaced about 3 mm from an adjacent protrusion.

Figure 16:
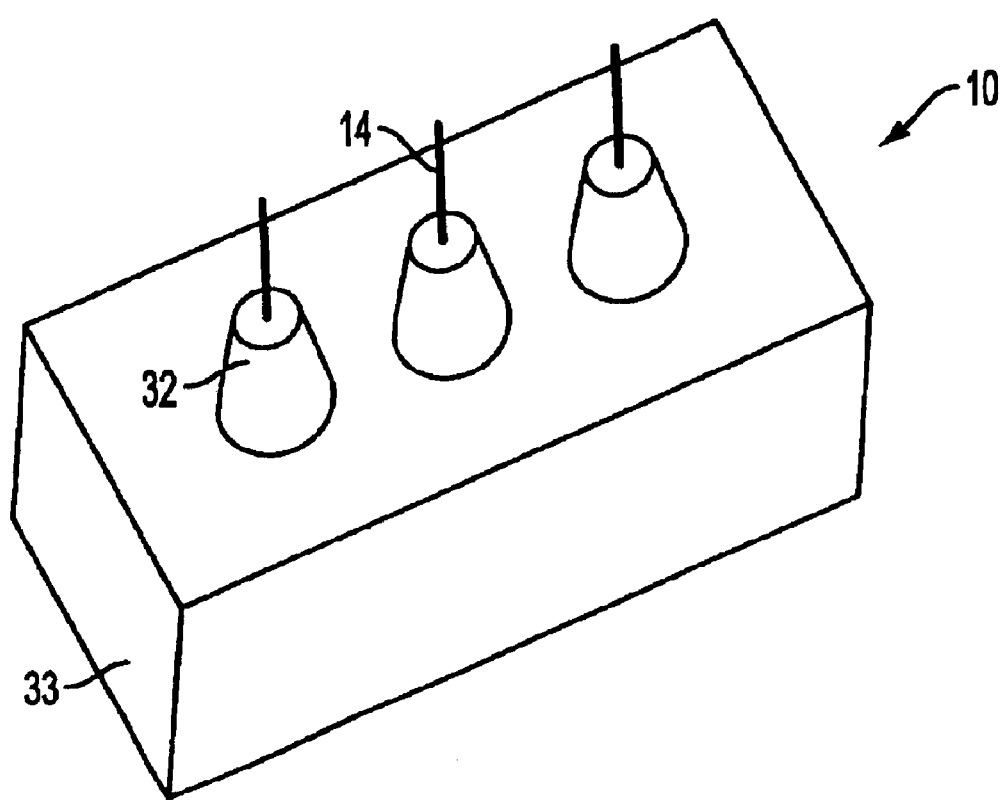
FIG. 16 is a perspective view of another embodiment of the dermal-access member array of the device.

Another embodiment of the dermal-access member array is shown in FIG. 16. It includes a linear dermal-access member array with a manifold 33 for holding the protrusions 32 and dermal-access members 14 having a rectangular face and a generally parallelpiped shape. Typically, the embodiment shown in FIG. 16 is integrated into device 10. Other than the protrusions, the embodiment of FIG. 16 has a planar face. The face can have a length of about 4.8 mm, and a width of about 11 mm. The protrusions have a linear arrangement and are spaced about 3 mm apart from one another. The diameter of the conical protrusions are relatively small, for example, about 0.95 mm or smaller.

The arrangement and relative heights of the dermal-access members, recesses, and protrusions can be modified to accomplish or emphasize any number of intended beneficial characteristics of the invention. Specifically, the length, width and spacing of the dermal-access members can vary depending on the pharmaceutical agent being administered or required to penetrate the skin to the optimum depth for the specific pharmaceutical or bioactive agent being administered. The device of the present invention maximizes the effective penetration of dermal-access members to a targeted depth. The device can control the size of the bleb. In a device with multiple dermal-access members, the device can be engineered to control the instillation patterning of individual blebs and their relationship to each other. Non-communication between individual dermal-access members can be meaningful for deposition of large volumes in a broad biological space or the deposition of multiple fluids, or in designing the pressure parameter of a dermal-access member. The device can be designed to provide sufficient fluid flow path to accommodate the desired velocity and rate of fluid to be instilled and to minimize the amount of void volume. The device can further be designed as a function of the desired bleb pattern and for application of a particular fluid at a particular site to minimize the area of application.

Generally, the patterning of the dermal-access members can be designed to achieve desired characteristics. Typically, a minimal number of dermal-access members can be used to reduce the pain or the perception of pain by a subject, manufacturing complexity or cost, the number of potential failure points, the complexity of the device fluid dynamics, and the dose lost to void volumes in the device or system. The number of dermal-access members can be increased to decrease the possibility of blocked fluid paths, to increase the distribution area of instilled fluid to accommodate a greater volume or delivery rate, and to potentially increase uptake.

Alternate arrangements for delivering fluid to the dermal-access members include but are not limited to multiple reservoirs; a manifold arrangement in which fluid is communicated from a reservoir, through individual channels to the dermal-access members; and independent channels. In addition, the channels can be provided with individual or combination valving or other means for fluid flow rate control.

As discussed above, the number and arrangement of dermal-access members and protrusions in each of the embodiments can depend on the desired range of fluid delivery volume. Furthermore, the recessed second surface area surrounding each protrusion can be arranged based on the desired range of fluid delivery volume. For example, a three member array that delivers 100 µl of fluid may have recesses surrounding each dermal-access member of approximately 5 mm in diameter. Conversely, a single member array that delivers 100 µl of fluid may have a recess surrounding the single dermal-access member with an approximately 10 mm diameter. As discussed above, the size and arrangement of the recesses depend on the desired flow characteristics, including the volume and rate of delivery of the substance.

A method for delivering or withdrawing a substance through the skin is also provided. The device is positioned in a target site on the surface of a subject's skin. The body is pressed downwardly against skin with a pressure sufficient to cause dermal-access members to penetrate the layers of skin. The depth of penetration is dependent upon the length of dermal-access members, the spacing of the dermal-access members, and the dimensions of the body, including the height of the protrusion, pressure exerted on the device, and the tensioning of the skin resulting from the body.

The skin of a subject has elastic properties that resist penetration by the dermal-access members. The skin can be stretched by the raised first surface area until the skin is taut before the dermal-access members penetrate the skin. A penetrating pressure can be applied to the device until the first surface area contacts the skin. This promotes uniform penetration of the skin by each of the dermal-access members. Consequently, when the device is secured to skin with either a manual application or adhesive, a pressure is constantly applied to dermal-access members 14.

A substance is supplied to the device and fed to dermal-access members for delivery to the subject. In alternative embodiments, a substance is withdrawn from the subject in a similar manner.

For a bolus type injection, the spacing of the delivery points is not as important because the pressure is higher and delivery occurs at each dermal-access member approximately simultaneously. Dermal-access member spacing in the bolus type injection may determine whether a single bleb or multiple blebs form.

For lower rate deliveries, it is beneficial to ensure that the delivery points are spaced close enough together to create a single bleb. As delivery at a particular dermal-access member in a multi-dermal-access member device begins, the pressure at that particular dermal-access member decreases. At relatively low delivery pressures, if the dermal-access members are spaced too far apart, the first dermal-access member to form a bleb will be the preferential path because the substance to be delivered will inherently follow the path of least resistance. Thus, by having all the points feed the same bleb, no preferential flow through a particular dermal-access member or delivery point should occur because pressure will be equalized across the dermal-access members.

The device of the invention can remain interfaced with the skin for sufficient time to withdraw from or deliver to the subject the desired substances. The length of time the device is required to be attached or in communication with the skin of the subject is usually dependent on the substance being delivered or withdrawn, the volume of the substance, the target area on the skin, the depth of penetration, and the number and spacing of dermal-access members. The amount of time the device is secured to the skin may reduce the amount of leakage from the skin after delivery of the fluid.

Many of the considerations in designing the device of the present invention involve proper placement of the dermal-access members, including placement of the dermal-access members at the proper depth. Specifically, pharmacokinetics (PK) for certain classes of medicaments can be improved by administering the medicament at a specified place below the stratum corneum.

Generally, deposition in intradermal tissue results in faster drug onset kinetics for system uptake and bioavailability, and increased bioavailability for some drugs. However, intradermal delivery is limited in that intradermal tissue space is highly compact and has limitations on the total amount of volume which can be administered, the rate at which such fluid can be administered, and the pressure required to administer such volume. Generally, the subcutaneous layer is not well perfused by capillaries. As such, absorption is both slower, and in some cases, decreased bioavailability.

Thus, the PK outcome of dermal-access delivery is specific to the deposition depth and patterning of the administered fluid and such deposition can be mechanically controlled via design of the device of the present invention. It has been shown that delivery of medicaments to two different depths increases the PK benefits, for example, delivery to both shallow subcutaneous areas and intradermal areas.

The present invention can include a device to deliver the medicament to two different depths, and specifically, to two different physiological tissue compartments, such as shallow subcutaneous and intradermal. This can be accomplished, for example, by dermal-access members of different lengths. Other geometric or mechanical mechanisms can also be designed to deliver fluids to different depths. The device can also be provided with flow restrictors to deliver differing amounts of fluid to different areas.

For each of the embodiments discussed herein, the device is optionally radiation stable to allow for sterilization, if radiation is to be used. Optionally, the body should be transparent or translucent to allow for light to penetrate and cure the UV adhesive holding the dermal-access member secure. As another option, the body can be opaque and epoxy can be used to secure the dermal-access member. It is noted that having a transparent body enables a user or other person administrating the device to properly prime the device by ensuring that no excess air is in the device. Furthermore, the body and cover portion material should be stiff enough so as not to deflect during normal use conditions and should be able to withstand internal fluid pressure in the range of about 2–5 psi to about 200 psi without failure or leaks. However, the flange and adhesive can be as flexible as necessary for comfortable and secure attachment to the subject. The body and cover portion material can selected to be non-affected by the drug and having no effect on the drug candidates to be used. The body and the cover portion material should also be hypoallergenic.

The device of the invention can optionally be used as a disposable, single-use device. The device can be sterilized and can be stored in a suitable sterile package.

Adequate dermal-access member seating is an important aspect of the present invention. Successful dermal-access member seating is defined as positioning the dermal-access members in the skin such that fluid delivered through the dermal-access member or dermal-access members does not leak out of the skin.

Generally, there are four factors which contribute to a desirable dermal-access member seating: dermal-access member length, dermal-access member protrusion geometry, dermal-access member overtravel, and the dermal-access member seating velocity. Overtravel is defined as the extent that the upper face of the protrusion extends beyond the adhesive or other securing mechanism of the device i.e., the bottommost face of the device. The embodiment shown in FIG. 12 has an overtravel of about 1 mm, although more or less overtravel amounts can be adequate to ensure proper dermal-access member seating, for example, about 0.5 mm. Of course, it is also important to avoid any obstructions on the body face.

Exemplary embodiments of the geometry of the device in general and of dermal-access member manifolds have been discussed above.

Experiments have shown that smaller protrusion diameters increase the effectiveness of dermal-access member seating. It was believed that the higher local pressure exerted by the smaller surface of the protrusion for a given force contributes to the beneficial dermal-access member seating.

It is further believed that the smaller surface area of the face of the protrusion has a smaller local effect on the development of the bleb.

In one such experiment, a device was applied to a swine test subject to determine the effectiveness of smaller diameter protrusions as compared to larger diameter protrusions. The experiment was conducted at a constant delivery pressure of 15 psi, with a 50 µL air bolus, and with needles as the dermal-access members. The protrusions are conical protrusions with a flat top surface. The dermal-access members extend 1 mm above the top surface of the protrusion. Although the surface is flat in this experiment, as noted above, the top surface of the protrusion can be concave or convex. If the top surface is concave, the length of the dermal-access member is measured from the outer rim of the top surface to the top of the dermal-access member. If the top surface is convex, the length of the dermal-access member is measured from the uppermost tangent of the surface to the top of the dermal-access member.

In the aforementioned experiment, the smaller diameter protrusions are about 1 mm (0.0375") in diameter and the larger diameter protrusions are about 2 mm (0.075") in diameter. The experiment also accounted for varying amounts of overtravel. The results are shown in FIG. 17. Column "over" describes the amount of overtravel in thousandths of an inch. Column "leaker" states whether the trial leaked or not. Column "bleb type" describes the number and particulars, if any. Column "average rate" describes the average steady-state flow rate calculated in µL/min. The average rate of a trial that leaked is 0. Column "if no leaks" shows the average rate of the properly seated trials.

As can be seen from FIG. 17, the smaller diameter protrusions provided better needle seating. In addition, overtravel was shown to be a factor in needle seating. The experiment suggested that overtravel greatly prevents leaking.

Interestingly, overtravel did not seem to negatively affect infusion rates. This was somewhat surprising, given the previous experience with overdriven or overtraveled needles. It has been the conventional experience when using 1 mm needles mounted in catheter tubing that pushing the catheter into the skin significantly affects the pressure required to infuse at a given rate in a constant pressure system. However, the amount of overtravel necessary to produce this effect is likely larger than the maximum overtravel of 0.040" seen in this experiment. This suggests an optimal overtravel amount which can be discerned from further experiments.

It has further been shown that an increased velocity in the application of the dermal-access members can increase the effectiveness of the seating.

An applicator for mechanically applying the device to a patient can control the velocity of the dermal-access members. For example, an applicator such as a Minimed SOF-SERTER™ insertion device or a BD INJECT-EASE™ device can be modified to apply the device to a user at a desired velocity. The device is driven toward the skin by springs contained in the applicator and results in the dermal-access members seating into the skin of a subject. Among other factors, the strength of the springs determines the velocity of the dermal-access members.

Experiments have shown that there is a continuum of velocity ranges within which dermal-access member seating improves with velocity, for a given skin type, manifold mass, and needle sharpness.

Initial seating experiments in Yorkshire pigs utilized a single spring rate of about 5 lbf/in. This allowed a 1.7 gram manifold to be propelled at about 6.3 m/s. At this velocity, most 1 mm and 3 mm dermal-access members seated without leaking. However, a large number of manifolds did not have enough energy to seat the dermal-access members to the required depth. Heavier manifold tests, from a drop-center design, had velocities of about 3 m/s. At this velocity, most of the 1 mm dermal-access members leaked. Similarly, most of the 3 mm dermal-access members produced very shallow blebs. One manifold arrangement uses two springs with spring constants of 3.2 lb/in, and is less massive than other manifolds. This manifold arrangement enables a manifold velocity of about 12 m/s or greater. With this arrangement, nearly 100% of the dermal-access members seated properly. Accordingly, it has been shown that, for this arrangement, a velocity of about 6 m/s to 18 m/s is ideal, optionally about 6 m/s to about 25 m/s. It is noted, however, that these resultant, calculated velocities were calculated based on energy conservation equations based on known initial forces, and does not account for any friction within the applicator or friction of the dermal-access members passing through the skin. The actual velocities in this example could be much less, for example, 50% less.

One experiment determining dermal-access member velocity utilizes a mechanical applicator in which a device with a three dermal-access member manifold is loaded. In this experiment, 34 gauge dermal-access members are used. A coil spring is placed on a post of the manifold to tension the manifold in the applicator. A luer and line arrangement can supply fluid to the manifold at a constant pressure. The applicator is placed on a swine, the applicator is activated to release the spring to drive the manifold with the dermal-access members into the skin, and fluid is delivered to the subject. In this experiment, the manifold is driven about 5 mm. The following parameters were considered:

Springs Force: None;
   Low: 1 lb. initial spring force, 0.5 lb. final force; or
   High 2 lb. initial spring force, 1 lb. final force
Device: Center or Side
Adhesive: Full or Missing (safety)
Septum: With or Without
Member Length: 1 mm or 3 mm The results are shown in FIGS. 18A–D. As can be seen, needle seating increases with velocity.

The following is a description of a further experiment demonstrating the importance of dermal-access member velocity. The tests were conducted to determine the more effective dermal-access member seating arrangement between a side push microinfuser and a drop-center infuser. The drop-center manifold ("heavy") weighs about 7.8 grams, and the side push manifold weights about 0.4–0.6 g. Therefore, for a given spring or spring set used to drive the manifold, the drop-center design will be at least 10 times slower in its initial velocity than the side push design. For this experiment, manifolds weighing about 1.7 grams were used as "light" manifolds. The results are shown in FIG. 19. For the 3 mm dermal-access members, the light manifolds had an average flow rate of about 3 times than that of the heavy manifolds. This indicates that for the 3 mm needles, the heavy manifold seated the needles to a considerably shallower depth than the light manifold. This is because shallower infusions are known to have a higher back pressure than deeper infusions. The differences shown in the 1 mm dermal-access members were even greater, and none of the heavier 1 mm manifolds were successfully seated.

The lack of obstructions on the face of the device has also been shown to increase effective dermal-access member seating. For example, the exemplary embodiment shown in FIG. 16 has a single surface, i.e., without the raised or recessed first or second surface areas discussed in previous embodiments. The effectiveness of needle seating for an obstructionless device face was shown in a further experiment. The device of FIG. 16 was incorporated into a mechanical applicator for applying the device to a subject at a constant pressure, constant volume, constant dermal-access member length and constant overtravel amount. The leakage rates for these trials were compared to those of trials using a device identical to that shown in FIG. 16, except that the device had walls extending around the periphery of the bottom face of the device, flush with the walls of the parallepiped shaped and at a height equal to that of the tops of the protrusions. The device with the walls leaked more often than the device without walls. It was determined that the presence of a wall on the device only hurts infusion reliability. It is believed that the wall limits the amount of overtravel of the device, and further, prevents the skin in the immediate proximity of the protrusions from wrapping around the protrusions. This agrees with the results of the experiment depicted in FIG. 17 and discussed above.

While various embodiments have been chosen to illustrate the invention, it will be appreciated by those skilled in the art that various additions and modifications can be made to the invention without departing from the scope of the invention as defined in the appended claims. For example, the body of the device may be made as an integral one-piece unit. In alternative embodiments, the body can be made from separately molded sections or pieces and assembled together. The molded sections can be assembled using an adhesive, by welding, or by the use of mechanical fasteners. Additionally, any number of dermal-access members may be provided on the device.

What is claimed is:

1. An apparatus for delivering or withdrawing a fluid through at least one layer of the skin of a subject, the apparatus comprising:

a device comprising a body having a top face, a bottom face spaced from the top face, and a side edge, the body defining at least one channel, wherein the bottom face includes a first surface area and a second surface area adjacent to and recessed at a first distance from the first surface area, the bottom face further including at least one raised protrusion disposed on the second surface area, the at least one raised protrusion having a height from the first surface, and the height being greater than the first distance;

at least one dermal-access member provided in the at least one raised protrusion and being in fluid communication with the channel to deliver or withdraw the fluid, the at least one dermal-access member extending at least 1 mm from the at least one protrusion; and means for driving the device against the skin at a calculated speed of about 6 m/s to about 18 m/s.

2. The apparatus of claim 1, wherein the at least one raised protrusion is a conical protrusion with a flattened upper surface having a diameter of less than 2 mm.

3. The apparatus of claim 2, wherein the flattened upper surface has a diameter of about 1 mm.

4. The apparatus of claim 1, wherein the at least one dermal-access member extends about 3 mm from the at least one protrusion.

5. The apparatus of claim 1, wherein the driving means drives the device against the skin at a calculated speed of about 12 m/s.

6. The apparatus of claim 1, wherein the second distance is at least about 0.5 mm greater than the first distance.

7. The apparatus of claim 1, wherein the second distance is at least about 1 mm greater than the first distance.

8. The apparatus of claim 1, wherein said driving means includes a coil spring.

9. The apparatus of claim 1, wherein the device includes a plurality of protrusions and one dermal-access member is provided in each protrusion, and wherein the dermal-access member of a respective protrusion is of a different length from the dermal-access member of another protrusion, the lengths of the dermal-access members being of sufficient lengths to deliver or withdraw the fluid from a subcutaneous layer of the skin and an intradermal layer of the skin.

* * * * *